United States Patent [19]
Shoher et al.

[11] Patent Number: 4,764,116
[45] Date of Patent: Aug. 16, 1988

[54] PREFABRICATED PONTIC FOR A DENTAL BRIDGE

[76] Inventors: Itzhak Shoher, 50 Shlomo-Hamelech St., Tel-Aviv, Israel, 64386; Aharon E. Whiteman, 13 J. L. Perez St., Petach-Tikvah, Israel, 49206

[21] Appl. No.: 93,771

[22] Filed: Sep. 8, 1987

[51] Int. Cl.$^4$ ............................................. A61C 13/22
[52] U.S. Cl. ................................................... 433/180
[58] Field of Search ............... 433/180, 181, 182, 183, 433/213

[56] References Cited

U.S. PATENT DOCUMENTS 1,738,460  12/1929  Stark ..................................... 433/180

FOREIGN PATENT DOCUMENTS 791336  9/1935  France ............................... 433/180

Primary Examiner—Robert Peshock
Attorney, Agent, or Firm—E. Lieberstein

[57] ABSTRACT

The invention relates to the construction of a prefabricated pontic for use in constructing a dental bridge. The prefabricated pontic has a framework that is adjustable in that it is comprised of a plurality of pliable metal members which interconnect for an open skeleton framework including an elongated central member extending lengthwise from the mesial to the distal and at least two members having open ends which overlap the central member at the mesial and distal ends with the open ends being separable from each other for adjusting the framework.

7 Claims, 2 Drawing Sheets

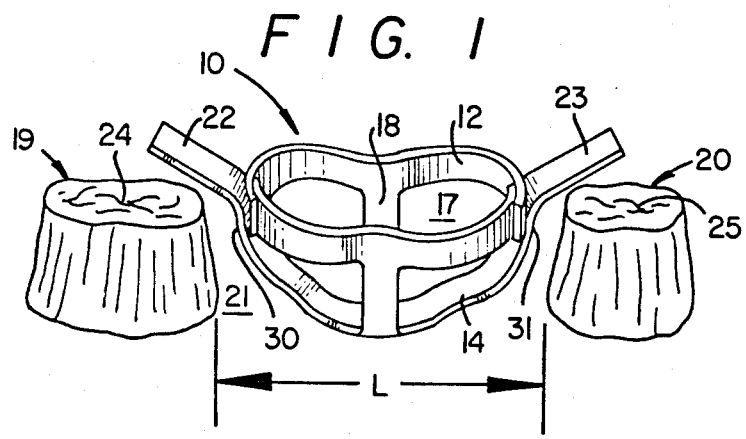
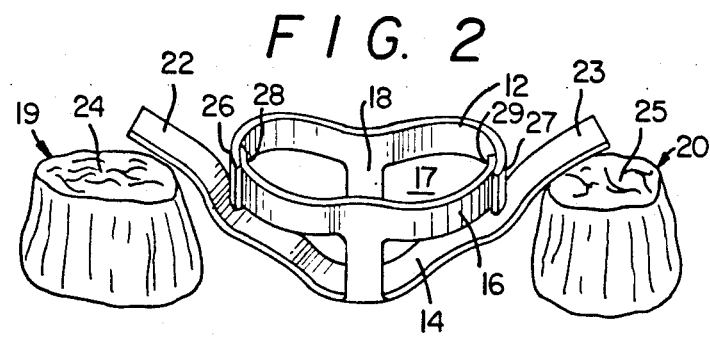
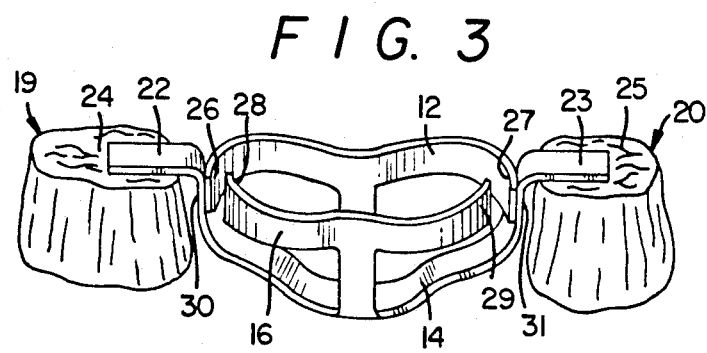

PREFABRICATED PONTIC FOR A DENTAL BRIDGE

This invention relates to the design of a prefabricated pontic for use in the construction of a dental bridge.

BACKGROUND OF THE INVENTION

A dental bridge is an artificial prosthesis used to replace at least one missing tooth between natural teeth. The bridge includes a pontic which fills the edentulous space and a connector to attach the pontic to the natural teeth for support.

In conventional practice, a dental bridge is cast from an intraoral impression of the teeth to be restored and its surrounding tissue. The cast bridge is custom made from a stone model of the dental impression taken of the patient. Casting a dental bridge involves a time consuming and complex procedure in which every detail must be meticulously followed to assure a proper fit. When the pontic and connector are cast, and usually in one piece, it is very difficult to make any adjustments to compensate for error.

Constructing a bridge from a prefabricated pontic and connector assembly offers the advantage of speed, simplicity and substantial cost savings over the cast bridge. However, the prefabricated assemblies of the past were either not strong enough to form a bridge, incapable of sustaining the biting forces in the mouth, or were too unwieldy to be accepted by the dental profession.

A technique has recently been developed for joining a prefabricated pontic of any design to abutment teeth to form a dental bridge of substantial strength without casting. This technique is disclosed in corresponding U.S. patent application Ser. No. 822,823 which relates to a dental prosthesis and method for aligning a prefabricated pontic having pliable arm rests between abutment teeth and securing the pontic by a welding operation. The arm rests extend from the pontic and permit the pontic to be adjusted into proper alignment relative to the abutment teeth. The arm rests are then spot welded to metal retaining members mounted upon the abutment teeth. Although this teaching overcomes earlier problems relating to the prior inability to align a prefabricated pontic between the teeth to be bridged too large a variety of different pontic sizes were still necessary to accommodate for differences in the size of the edentulous space between different teeth, particularly in length.

A prefabricated pontic has now been discovered which provides the dentist or dental technician with substantial freedom to adjust the pontic size to fit the edentulous space between abutment teeth so that a one size prefabricated pontic may be used in the construction of a dental bridge for most posterior teeth with the assurance that it can be adjusted to properly fit into the patient's mouth and conform to the patient's anatomy. Although the prefabricated pontic of the present invention may also be used for anterior restorations, it is particularly suited for constructing a posterior bridge where the pontic serves as a molar tooth. A posterior dental bridge requires maximum strength to resist the forces of mastication during chewing.

It is therefore the primary object of the present invention to provide a prefabricated pontic which has universal application in the construction of a dental bridge.

SUMMARY OF THE INVENTION

A prefabricated pontic having an adjustable framework adapted to fill the edentulous space between abutment teeth in the construction of a bridge comprising: a plurality of pliable metal members which interconnect in an arrangement to form an open skeleton framework including at least one elongated central member extending lengthwise from the mesial to the distal and at least two members having open ends which overlap said central member at the mesial and distal ends with said open ends being separable from each other and from said central member for adjusting said framework to fill the spac between said abutment teeth.

BRIEF DESCRIPTION OF THE DRAWINGS

Other objects and advantages of the present invention will become apparent from the detailed description of the invention when read in conjunction with the following drawings of which:

FIG. 1 is a perspective view of the prefabricated pontic of the present invention for constructing a dental bridge;

FIG. 2 is another perspective view of the prefabricated pontic of FIG. 1 shown in the process of being adjusted to fill up the empty space between the abutment teeth;

FIG. 3 is yet another perspective of the prefabricated pontic of FIG. 1 to show the progression in the adjustment of the pontic for filling the space between the abutment teeth;

DETAILED DESCRIPTION OF THE PREFERRED EMBODIMENTS

Figure 4:
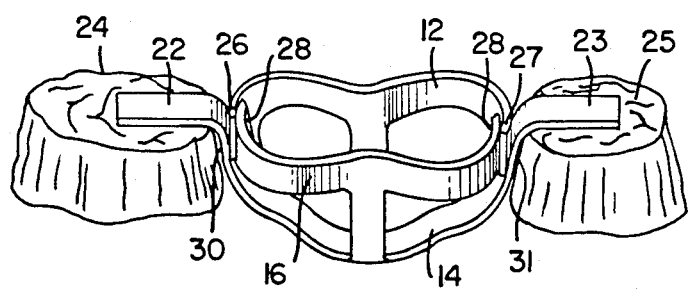
FIG. 4 shows in perspective the pontic of FIG. 1 fully adjusted into spacial alignment between the abutment teeth.

FIGS. 1–4 show the prefabricated pontic of the present invention being adjusted from a first position in FIG. 1 where it is too small to fit the edentulous spacing between the teeth to be bridged into a final position in FIG. 4 following a staged progression to fill the edentulous space before completing the construction of a dental bridge.

The prefabricated pontic 10 as shown in each of the FIGS. 1 to 4 comprises a plurality of pliable cross connecting metal members 12, 14, 16 and 18, which interconnect to form an open skeleton framework. The underlying concept of using an open framework of metal for a pontic as opposed to a solid mass is taught and described by Applicant in U.S. Pat. No. 4,231,740 which issued Nov. 4, 1980, the disclosure of which is herein incorporated by reference. This patent specifically relates to the fabrication of a metal under-structure from a wax pattern to form a crown or a metal pontic with a skeleton-like metal framework. The skeleton-like metal framework can take many different shapes depending upon the restoration to be formed. The pontic designs disclosed in the aforementioned patent are intended to be cast for use in fabricating single unit dental restorations particularly of porcelain to metal.

The central member 14 of the pontic 10 is a single continuous band of member which extends from the mesial to the distal relative to the abutment teeth 19 and 20. The open space between the abutment teeth 19 and 20 defines the edentulous space to be bridged with the prefabricated pontic 10. The central member 14 extends lengthwise to form arms 22 and 23 which overlie the occlusal surfaces 24 and 25 of the abutment teeth 19 and 20. In this position, the arms 22 and 23 will support the pontic 10 in a suspended position between the abutment teeth.

The metal member 12 is curved in an arch extending from the mesial to the distal along its buccal surface. The metal member 16 in a complementary fashion, is curved in an arch extending from the mesial to the distal along its lingual surface. The cross member 18 extends in an arch buccolingually to interconnect the members 12, 14 and 16. This forms a large occlusal concavity 17 which may be filled with a veneering material such as an acrylic or porcelain after the bridge is completed. The metal members 12 and 16 have open ends 26, 27, 28 and 29 which overlap and abut the metal member 14 at the mesial and distal ends 30 and 31 of the pontic 10 but are not fixedly attached to each other. Accordingly, the members 12, 14 and 16 may easily be separated one from the other at the mesial and distal ends 30 and 31, respectively. If the span length "L" between the abutment teeth is too long to properly seat the pontic 10, the framework dimensions of the pontic 10 may be readily modified to fit the space. Adjustment of the pontic is carried out in accordance with FIGS. 2 to 4 to conform the prefabricated pontic dimensions to the span length "L".

As shown in FIG. 2, the arms 22 and 23 are pulled apart using pliers for separating the central member 14 from the members 12 and 16 at the mesial and distal ends of the pontic. Each member 12 and 16 is then pulled outwardly as shown in FIG. 3 using for example a conventional 3 and/or 4 prong dental pliers. The pontic is reconfigured into a modified shape as shown in FIG. 4 with the open ends 26, 27, 28 and 29 realigned to overlap and abut the central member 14 at the mesial and distal ends 30 and 31 of the pontic 10. Thus, it is readily apparent that the pontic framework can be modified to fill the edentulous space 21 between abutment teeth over a wide variation in span length "L". The adjustment in pontic length may result in a small change in width which has little significance to the overall structure.

Once the pontic 10 is adjusted to conform to the spacing between the abutment teeth, it is removed and the open overlapping ends 26 and 28 at the mesial end 30 and 27 and 29 at the distal end 31 are united to form a strong solid joint either by welding, bonding or riveting. If the members are to be riveted together an elongated slot or hole may be formed along the overlapping ends of the members 12, 14 and 16 to effectuate the riveting operation. Thereafter, the pontic 10 is repositioned with the arms 22 and 23 suspended between the abutment teeth 19 and 20. The arms 22 and 23 may be attached to the abutment teeth in any conventional fashion to complete the bridge and form a fixed prosthesis. This is preferably accomplished by first mounting a retaining member upon each abutment tooth and then welding the arms to each retaining member.

Figure 5:
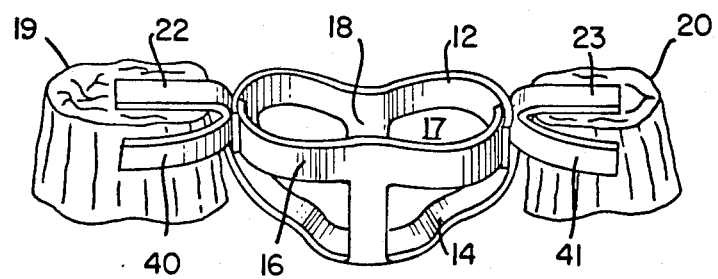
FIG. 5 is a perspective view of an alternate embodiment of the prefabricated pontic of FIG. 1 for constructing a bridge between two abutment teeth.

An alternative embodiment for the prefabricated pontic of the present invention is shown in FIG. 5 with corresponding reference numerals used to identify equivalence with the embodiment of FIG. 1 where applicable. The basic distinction lies in the use of additional arms 40 and 41 for wrapping the pontic at least partially around the buccal and lingual sides of the abutment teeth 19 and 20.

The composition of the metal members 12, 14, 16 and 18 for both embodiments is not critical to the present invention. However, the metal must be pliable so that the framework can be adjusted with the open overlapping ends of the members adjusted from one at rest position into another at rest position which is displaced from the first position. It is also necessary for the metal composition of the members to be compatible with the oral environment in which it is to be placed and accordingly, should preferably be composed of precious metals and alloys thereof. The metal members must also be of a composition which will provide desirable physical and structural characteristics for its use in a dental bridge.

Although any method of forming a pontic with a plurality of metal members as hereinbefore described may be used, the preferred method is a conventional stamping operation in which the cross connecting metal members 12, 14, 16 and 18 are punched out from a sheet of metal using a die.

What is claimed is:

1. A prefabricated pontic having an adjustable framework adapted to fill the edentulous space between abutment teeth in the construction of a bridge comprising: a plurality of pliable metal members which interconnect in an arrangement to form an open skeleton framework including at least one elongated central member extending lengthwise from the mesial to the distal and at least two members having open ends which overlap said central member at the mesial and distal ends with said open ends being separable from each other and from said central member for adjusting said framework to fill the space between said abutment teeth.

2. A prefabricated pontic as defined in claim 1 wherein said central member forms two arms for extending over the occlusal surface of each abutment tooth.

3. A prefabricated pontic as defined in claim 2 wherein one of said members with open ends extends mesial distally about the buccal surface and wherein another of said members with open ends extends mesial distally about the lingual surface.

4. A prefabricated pontic as defined in claim 3 further comprising a cross connecting metal member which lies buccolingually and interconnects the metal members extending mesial distally.

5. A prefabricated pontic as defined in claims 2 or 4 wherein said arrangement of metal members forms a large occlusal concavity.

6. A prefabricated pontic as defined in claim 8 with said plurality of metal members being integrally formed from a die stamping operation.

7. A prefabricated pontic as defined in claim 6 wherein each of said members is composed from precious metals.

* * * * *